US007815903B2

(12) United States Patent
Khan et al.

(10) Patent No.: US 7,815,903 B2
(45) Date of Patent: Oct. 19, 2010

(54) PROCESS FOR COMMERCIAL PRODUCTION OF BIOPESTICIDES

(75) Inventors: Mujeebur Rahman Khan, Aligarh (IN); Shahana Majid, Aligarh (IN); Fayaz Ahmad Mohiddin, Aligarh (IN); Nabilah Khan, Aligarh (IN)

(73) Assignees: Aligarh Muslim University, Aligarh (IN); Department of Biotechnology, New Delhi (IN)

(*) Notice: Subject to any disclaimer, the term of this patent is extended or adjusted under 35 U.S.C. 154(b) by 1174 days.

(21) Appl. No.: 11/393,246

(22) Filed: Mar. 30, 2006

(65) Prior Publication Data

US 2006/0292124 A1 Dec. 28, 2006

(51) Int. Cl.
*A01N 3/04* (2006.01)
*A01N 63/00* (2006.01)
*G01N 33/569* (2006.01)

(52) U.S. Cl. .................... 424/93.4; 424/93.5; 435/7.32; 435/7.31; 504/117

(58) Field of Classification Search ....................... None
See application file for complete search history.

(56) References Cited

U.S. PATENT DOCUMENTS

| | | | | |
|---|---|---|---|---|
| 4,117,136 | A * | 9/1978 | Hisada et al. | 514/291 |
| 4,837,155 | A * | 6/1989 | Tabachnik | 435/256.8 |
| 5,332,673 | A * | 7/1994 | Harris et al. | 435/253.3 |
| 5,962,305 | A * | 10/1999 | Mihara et al. | 435/262.5 |
| 6,511,821 | B2 * | 1/2003 | Singh et al. | 435/42 |
| 2005/0182129 | A1 * | 8/2005 | Ikeda et al. | 514/450 |

FOREIGN PATENT DOCUMENTS

WO WO 2005/121314 * 12/2005

OTHER PUBLICATIONS

Siddiqui et al. (Journal of Plant Diseases and Protection; Mar. 2005; 112 (12): 146-155).*

* cited by examiner

*Primary Examiner*—Shanon A Foley
(74) *Attorney, Agent, or Firm*—The Webb Law Firm

(57) ABSTRACT

The invention relates to a process for producing biopesticides based on *Trichoderma harzianum*, *Pochonia chlamydosporia* and *Pseudomonas fluorescens* comprising preparing mass or stock culture of biocontrol fungi and bacteria on sawdust, soil and molasses mixture, and then immobilizing the bioagents in a flyable based carrier.

10 Claims, No Drawings

US 7,815,903 B2

PROCESS FOR COMMERCIAL PRODUCTION OF BIOPESTICIDES

FIELD OF INVENTION

This invention relates to a process to produce biopesticides using saw dust-soil-molasses as stock culture of bioagents and flyash to immobilise the bioagents. The process of the present invention is cable of producing three biopesticides based on *Trichoderma harzianum, Pochonia chlamydosporia* and *Pseudomonas fluorescens* to control fusarial wilt (caused by *Fusarium* spp.) root knot (caused by *Meloidogyne* spp.) and wilt disease complex (caused by *Meloidogyne+fusarium*) of legume crops.

PRIOR ART

Numerous biopesticides of *Trichoderma* spp. are known in the art. By and large, these biopesticides are developed on talc and because of white colour they are well differentiated from biofertilizers such as rhizobium which are based on charcoal and appear black. Because of the inert nature and noninfluence on the activity of microorganisms, talc is used in biopesticide formulations. But, due to absence of any nutrient in talc, the population (CFUs) of a bioagent in the formulation decreases considerably during storage and marketing. Probably for this reason the biopesticides generally available contain CFUs much less than $10^8$/g formulation. Often a formulation fails to give any CFU count, and it is suspected that a fungicide is mixed in the carrier. When such a formulation is inoculated on a medium in petriplate usually colony of other microorganisms also does not develop. Moreover, talc is comparatively expensive as a result the existing formulations are costly.

The major drawback in the existing technology of bipesticide production is that during storage and marketing population (CF/U) of the bioagent decreases. Talc as a carrier is used almost invariably to produce biopesticides. The talc is an inert material and does not promote multiplication of bioagents during storage and marketing. Rather a longer storage duration causes decrease in the viability of bioagent propagules. As a result the talc based formulation contains a much low CFU load than the standard of $10^8$ CFUs of fungi or $10^{10-12}$ CFUs of bacteria. It is obvious when such a biopesticide is applied a satisfactory management of the target disease does not occur.

OBJECTS OF THE INVENTION

An object of the present invention is to propose a novel process for producing biopesticides of biocontrol fungi and bacteria supports the survival as well as multiplication of the bioagents during storage at room temperature and marketing so that the formulation contains population of bioagents of $\geq 10^8$ or $10^{12}$ CFUs/g formulation.

Yet another object of the present invention is to propose a novel process for producing biopesticides of biocontrol fungi and bacteria, which has a growth medium for mass (stock) culture of bioagents and a carrier (immobilizer) available at low costs.

Still another object of the present invention is to propose a novel process for producing biopesticides of biocontrol fungi and bacteria, so as to provide efficacious biopesticides namely, Biowilt-X (*Trichoderma harzianum*), Bionem-X (*Pochonia chlamydosporia*) and Biocomp-X (*Pseudomonas fluorescens*) to control fusarial wilt (caused by *fusarium* spp.) root-knot (caused by *meloidogyne* spp.) and wilt disease complex (caused by *Meloidogyne+Fusarium*).

DESCRIPTION OF INVENTION

According to this invention there is provided a process for producing biopesticides based on *Trichoderma harzianum, Pochonia chlamydoosporia* and *Pseudomonas fluorescens* comprising in a first step of mass or stock culture of biocontrol fungi and bacteria prepared on saw dust, soil and molasses mixture, and a second step comprising in immobilization of the bioagents in a flyash based carrier.

The carrier comprises a mixture of flyash soil and molasses. The carrier is autoclaved and then inoculated with homogenized pure culture of the bioagent.

Pure culture of *Trichoderma harzianum* and *Pochonia chlamydosporia* is prepared in potato dextrose supplemented with a chloramphenicol and *Pseudomonas* fluorescent in Kings B broth supplemented with novobiocin, penicillin and cycloheximide. The pure bioagent with said autoclaved mixture is subjected to the step of incubation. The mixture of sawdust soil and molasses is autoclaved and then innoculated with homogenized pure culture of the bioagent.

EXAMPLE-1

STEP I; Production of Mass/Stock Culture of Bioagents

Various agricultural and waste materials viz., seed husk-soil-molasses, saw dust-soil-molasses, baggasse-soil-molasses, leaflitter-molasses, sorghum meal-molasses and sorghum seeds were tested for mass production of biocontrol fungi and bacteria. Based on relative performance of the material tested, sawdust-soil-molases (5%) mixture in the ratio of 15:5:1 was selected to grow mass (stock) culture of bioagents viz., *Trichoderma harzianum, Pochonia chlamydosporia* and *Pseudomonas fluorescens*. One kg of the mixture was filled in heat resistant polybags. The bags were sealed and steam sterilized at 15 kg/cm$^2$ pressure at 121° C. for 15 minutes. For *trichoderma harzianum* and *pochonia chlamydosporia*, chloramphenicol 10 mg/kg material and for *P. fluorescens* 45 mg novoboicin, 44.9 mg penicillin and 75 mg cycloheximide was added to the 1 kg material. There after the bags containing 1 kg autoclaved sawdust-soil-molasses mixture were inoculated with homogenized pure culture of the bioagent (5 ml/bag) by sterilized needle and syringe. A puncture made in the polybag to insert the needle was released by cellotape. Pure culture of *Trichoderma harzianum* and *Pochonia chlamydosporia* were prepared in potato dextrose broth supplemented with chloramphenicol 10 mg/litre and pseudomonas fluorescens in Kings B broth supplemented with 45 mg novobiocin, 44.9 mg penicillin and 75 mg cycloheximide per litre. The bag was resealed and incubated at room temperature (30-35° C.) or at 25±2° C. in an incubator for 10-15 days (fungi) and 35±2° C. for 5 days (bacteria) in an incubator. During incubation the bag were shaken daily for a few minutes to achieve uniform colonization by the bioagents on the material. Luxurient and uniform colonization by the bioagents occurred with in the incubation duration of 5-15 days.

STEP II: Immobilization of Bioagents

After preliminary screening of molasses-lignite-stillage granules, alginate-bran-fermenter biomass pellets, alginate-clay pellets, diatomacious molasses-soil pellets, sawdust-soil-molasses fermenter biomass, seek husk-sand-molasses fermenter biomass.

charcoal powder/pyrex (talc) fermentor biomass powder, fly ash fermenter biomass powder, sodium alignate pellets of liquid fermenter biomass etc., to support survival and multiplication of biocontrol fungi and bacteria four carriers viz., talc, charcoal, fine clay and flyash were selected for further study (FIG. 1 of the accompanying drawings). The stock culture of biocontrol fungi viz., *Trichoderma harzianum* and *Pochonia chlamydosporia* was mixed in the above mentioned four carriers and 5% molasses in the ratio of 1:0:1, 1:5:1, 1:10:1, 1:15:1 and 1:20:1 and supplemented with 10 mg chloramphenicol/kg formulation and was incubated at $25\pm2°$ C. in an incubator for 10 days. For pseudomonas fluorescens the carrier was supplemented with novobicoin (45 mg), penicillin (44.9 mg) and cycloheximide (75 mg/kg carrier) and then mixed with the stock culture and incubated at $35\pm2°$ C. for 15 days. After incubation CFU load/g formulation was determined using the dilution plate method which has been presented in FIG. 1. The fly ash based formulation revealed highest CFU count in comparison to the other materials used. The CFU load of *T. harzianum, P. chlamydosporia* and *P. fluorescens* on fly ash was increased by 31-117%, 19-40% and 23-71% in fly ash compared to the stock culture or other carriers, respectively (FIG. 1).

Final Composition of the Biopesticides

A mixture of flyash, soil (loam) and 5% molasses in the ratio of 15:3:1 plus chloramphenicol formulation for biocontrol fungi or 45 mg novobiocin, 44.9 mg penicillin and 75 mg cycloheximide formulation for biocontrol bacteria was used as a carrier to immobilize *Trichoderma harzianum, Pochonia chlamydosporia* and *Pseudomonas fluorescens*. The fly ash was collected from a coal fired thermal power station, Kasimpur, Aligarh, where bituminous coal is burnt. Some of the important physico-chemical characteristics of the ash were: pH 8.9, conductivity 7.6 m mhos/cm, cation exchange capacity 9.3 m mhos/cm, sulphate 9.72%, carbonate 1.07%, bicarbonate 2.60%, chloride 1.85%, nitrogen 0.00%, phosphorus 0.093%, potassium 0.82%, calcium 1.06%, magnesium 0.90%, manganese 64.5 mg/g, copper 117.8 mg/g, zinc 85.1 mg/g and boron 198.5 mg/g. The ash soil mixture was solarized under thin and transparent polythene sheet for five days (+38° C. ambient temperature) or filled in heat resistant polybags and autoclaved at 15 kg/m$^2$ pressure at 121° C. for 15 minutes. Thereafter, 1 part stock culture was added to the bags containing 20 parts carriers (ash-soil mixture) and shaken for uniform distribution. The bags were sealed and incubated for 10-15 days at room temperature (25-35° C.) or inside an incubator at $25\pm2°$ C. for *T. harzianum* and *P. chlamydosporia* and $35\pm2°$ C. for *P. fluorescens*. After incubation number of colony forming units (CFUs)/g formulation was determined using dilution plate method. The ratio of 20 parts carrier and one part stock culture was found to be the best in comparison to 5:1, 10:1 and 15:1. The formulations were packed in airtight polypacks of 200, 500 and 1000 g.

Shelf Life

Shelf life of the three biopesticides was tested at five temperature regimes i.e., 5° C., 10° C., 15° C., 25° C. and ambient (March) for 32 weeks (FIG. 2). The biocontrol fungi and bacteria (bioagents) not only remained viable during storage but also multiplied, evidenced by a much greater CFU load during the storage. The CFU load of the bioagents during storage is summarized separately under the following headings supported by FIG. 2.

BIOWILT-X (*Trichoderma harzianum*): At ambient temperature, the CFU count of *Trichoderma harzianum* increased significantly in comparison to other temperatures, next was 25° C. Greatest CFU load/g formulation ($10^{10}$) was recorded during 4 to 12 weeks (FIG. 5). From $12^{th}$ week onwards, the CFU count gradually declined but even at $16^{th}$ week of storage it was greater than the control at 25° C. or ambient temperature. The fungus was, however, detected in the formulation upto 32 weeks (FIG. 2)

Bionem-X (*Pochonia chlamydosporia*): The CFU count of *Pochonia chlamydosporia* in the formulation was greater during 14 weeks ($10^9$) and reached a peak ($3$-$4\times10^9$) at $10^{th}$ or $12^{th}$ week at 25° C. or ambient temperature (FIG. 2). Thereafter, the CFU count drastically decreased but still it was at par with the control at $32^{nd}$ week of storage at 25° C. or ambient. At rest of the temperature regimes, the biocontrol fungus was not detected after 14 weeks (FIG. 2).

Biowilt-X (*Pseudomonas fluorescens*): The CFU load of Pseudomonas fluorescens increased from first week reaching to its peak at 2-12 weeks ($9$-$12\times10^{13}$) at 25° C. or ambient temperature (FIG. 5). From $12^{th}$ week onwards it gradually decreased to a minimum at the $32^{nd}$ week, but still equal to the control. At rest of the temperatures the CFU load was much low (FIG. 2).

EXAMPLE 2

Field trials were conducted during two consecutive years to test effectiveness of the three biopesticides, namely Biowilt-X (*Trichoderma harzianum*), Bionem-X (*Pochonia Chiamydosporia*) and Biocomp-X (*Pseudomonas fluorescens*) was tested against the target diseases, wilt (*Fusarium oxysporum* f.sp. *ciceri* and *F. Udum*), root-knot (*Meloidogyne incognita*) and wilt disease complex (*Fusarium+Melodiogyne*) on chikpea and Pigeonpea. Performance of the biopesticides was compared with effecacious fungicide (carbendazim) and nematicide (nemacur) and their mixture (carbendazim+nemacur). The field soil was in-fested with $10^6$ colony forming units (CFU) of *Fusarium* spp. per g soil and/or 2000 juveniles of *M. incognita* per kg soil. The biopesticides were applied to the seeds of chickpea and pigeonpea at a dose of 2 g/kg seeds along with the rhizobium. The crops were harvested four months of sowing. During the trials, soil populations of the pathogens and bioagenst were monitered monthly. The cost-benefit ratios were calculated considering an exaggerated cost of biopesticide application (Rs.500/ha). Summary of the observations recorded during the trial is as follows.

1. Application of Biowilt-X (*Trichoderma harzianum*) and Bionem-X (*Pochonia chlamydosporia*) satisfactory controlled fusarial wilt (*Fusarium* spp.) and root-knot diseases (*Melodogyne* spp.), respectively. This treatment gave a profit of Rs.3180-8140/ha depending on the disease and crop as indicated in the following table.

| Biopesticide | Disease | Chickpea | Pigeonpea |
| --- | --- | --- | --- |
| Biowilt-X | Fusarial wilt | 4.2 q = Rs.6220/ha | 4.8 q = Rs.8140/ha |
| Bionem-X | Root-knot | 2.3 q = Rs.3180/ha | 2.6 q = Rs.4180/ha |

2. Seed treatment with Biocomp-X (*Pseudomonas fluorescens*) was highly effective against wilt disease complex (*Fusarium+Melodogyne* spp.) of chickpea and pigeonpea. The biopesticides also controlled fusarial wilt and root-knot diseases satisfactorily. Application of the Biocomp-X gave a profit of Rs.3460-11980/ha depending on the disease and crop as indicated in the following table.

| Disease | Chickpea | Pigeonpea |
| --- | --- | --- |
| Fusarial wilt | 3.9 q/ha = Rs.5740/ha | 4.1 q/ha = Rs.6880/ha |
| Root-knot | 2.3 q/ha = Rs.3500 | 2.2 q/ha = Rs.3460/ha |
| Disease complex | 7.8 q/ha = Rs.11980/ha | 6.2 q/ha = Rs.10660/ha |

3. Application of the biopesticides resulted to 40-68% decrease in the soil population of wilt fungus (*Fusarium* spp.) and root knon nematode (m/incognita). The bioagents established in the soil evidenced by 60-90% increase in their soil populations, and confered long lasting and ecofriendly disease management.

The invention claimed is:

1. A process for producing biopesticides derived from *Trichoderma harzianum, Pochonia chlamydosporia* and *Pseudomonas fluorescens* said method comprising preparing mass or stock culture of biocontrol fungi and bacteria on saw dust, soil and molasses mixtures, and then immobilizing the biocontrol fungi and bacteria in a flyash based carrier.

2. The process as claimed in claim 1, wherein a pure culture of *Trichoderma harzianum* and *Pochonia chlamydosporia* is prepared in potato chloramphenicol and wherein a culture of *Pseudomonas fluorescens* is prepared in Kings B broth supplemented with a supplementing agent selected from the group consisting of novobiocin, penicillin and cycloheximide.

3. The process as claimed in claim 1, wherein the stock culture of biocontrol fungi is mixed with flyash and a supplementing agent and subjected to the step of incubation.

4. The process as claimed in claim 1, wherein the mixture of saw dust, soil and molasses is autoclaved and then inoculated with a homogenized pure culture of the biocontrol fungi and bacteria.

5. The process as claimed in claim 2, wherein the carrier comprises a mixture of flyash, soil and molasses.

6. The method as claimed in claim 5, wherein the saw dust, the soil and the molasses are present in the mixture in a ratio of 15:5:1 or 15:3:1.

7. The process as claimed in claim 2, wherein said mixture is autoclaved and then inoculated with homogenized pure culture of the biocontrol fungi and bacteria.

8. The process as claimed in claim 7, wherein the pure biocontrol fungi and bacteria with said autoclaved mixture is subjected to the step of incubation.

9. A method for the effective control of the diseases fusarial wilt, root-knot and wilt disease complex of chickpea and pigeonpea comprising applying biopesticides selected from the group consisting of *Trichoderma harzianum, Pochonia chlamydosporia* and *Pseudomonas fluorescens* and combinations thereof.

10. The method as claimed in claim 9, wherein control of the disease chickpea and improved yield of pigeonpea is 18-56% and 16-44%, respectively.

* * * * *

UNITED STATES PATENT AND TRADEMARK OFFICE
CERTIFICATE OF CORRECTION

PATENT NO. : 7,815,903 B2
APPLICATION NO. : 11/393246
DATED : October 19, 2010
INVENTOR(S) : Khan et al.

It is certified that error appears in the above-identified patent and that said Letters Patent is hereby corrected as shown below:

Title Page, insert:
Item -- (30)   Foreign Application Priority Data
June 22, 2005      (IN) ................................ 1621/DEL/2005 --

Column 6, Line 8, Claim 5, "as claimed in claim 2," should read -- as claimed in claim 1, --

Column 6, Line 13, Claim 7, "as claimed in claim 2," should read -- as claimed in claim 5, --

Signed and Sealed this
Twenty-sixth Day of July, 2011

David J. Kappos
*Director of the United States Patent and Trademark Office*